United States Patent [19]

Rothgery

[11] 4,306,988
[45] Dec. 22, 1981

[54] SELECTED POLY(OXYALKYLATED) 1,3,4-THIADIAZOLES AND THEIR USE AS CORROSION INHIBITORS

[75] Inventor: Eugene F. Rothgery, North Branford, Conn.

[73] Assignee: Olin Corporation, New Haven, Conn.

[21] Appl. No.: 205,557

[22] Filed: Nov. 10, 1980

[51] Int. Cl.³ .................................................. C23G 1/06
[52] U.S. Cl. ..................... 252/150; 252/148; 252/149; 252/151; 252/391; 134/41; 422/12; 422/16
[58] Field of Search ............... 252/150, 149, 148, 151, 252/391; 422/12, 16; 134/41

[56] References Cited

U.S. PATENT DOCUMENTS

| | | |
|---|---|---|
| 2,518,109 | 8/1950 | Zerbe . |
| 2,544,001 | 3/1951 | Zerbe . |
| 2,547,193 | 4/1951 | Zerbe . |
| 3,966,623 | 6/1976 | Krug .............................. 252/391 X |
| 4,128,510 | 12/1978 | Richwine . |
| 4,136,043 | 1/1979 | Davis ............................... 252/391 X |
| 4,193,882 | 3/1980 | Gemmill, Jr. .................... 252/391 X |

*Primary Examiner*—Mayer Weinblatt
*Attorney, Agent, or Firm*—William A. Simons; Thomas P. O'Day

[57] ABSTRACT

Disclosed are selected poly(oxyalkylated) 1,3,4-thiadiazoles of the formula:

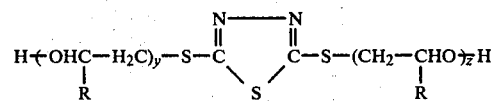

wherein each R is individually selected from hydrogen and methyl; and the sum of y and z is from 2 to about 30. These compounds are shown to be effective corrosion inhibitors in corrosive liquids such as acid metal-treating baths.

10 Claims, No Drawings

SELECTED POLY(OXYALKYLATED) 1,3,4-THIADIAZOLES AND THEIR USE AS CORROSION INHIBITORS

BACKGROUND OF THE INVENTION

1. Field of the Invention

This invention relates to selected poly(oxyalkylated) 1,3,4-thiadiazoles and their use as corrosion inhibitors.

2. Description of the Prior Art

The prior art has disclosed a wide variety of chemical compounds which effectively reduce the corrosive properties of liquids such as acid metal-treating baths. These inhibitors are generally added to the corrosive liquids to protect the metals in contact with these liquids. Alternatively, such inhibitors may be applied to the metal surface, either as is, or as a solution in some carrier liquid or paste.

While many of these corrosion inhibitors have been used successfully for many years, stricter toxicological and other environmental standards are restricting the use of some of the compounds (e.g., chromates and dichromates). Accordingly, there is a need in the art to develop new and effective corrosion inhibitors which do not pose these environmental problems.

BRIEF SUMMARY OF THE INVENTION

The present invention is directed to the use of poly(oxyalkylated) 2,5-dimercapto-1,3,4-thiadiazoles of the formula (I):

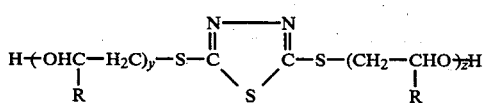

wherein each R is individually selected from H and $CH_3$; and the sum of y and z is from 2 to about 30, as corrosion inhibitors, particularly in acid metal-treating baths.

DETAILED DESCRIPTION

The poly(oxyalkylated) adducts of 2,5-dimercapto-1,3,4-thiadiazole may be made by reacting the 2,5-dimercapto-1,3,4-thiadiazole with two or more moles of either ethylene oxide, propylene oxide, or mixtures thereof [either sequentially or mixed together]. The general reaction for making these adducts is illustrated by the following Equation (A) wherein 2,5-dimercapto-1,3,4-thiadiazole (DMTD) is reacted with 5 moles of propylene oxide to produce the desired 2,5-dimercapto-1,3,4-thiadiazole.5 propylene oxide adduct product:

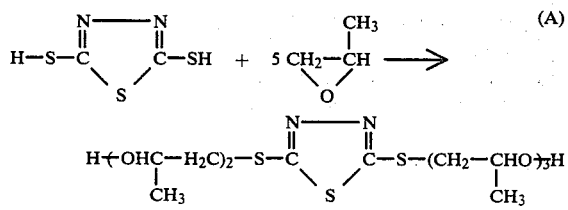

The 2,5-dimercapto-1,3,4-thiadiazole reactant may be conveniently made from hydrazine, sodium hydroxide, and carbon disulfide as described in Beilstein, EII-27, page 761 and in Example 1 of U.S. Pat. No. 4,128,510 which issued to Richwine on Dec. 5, 1978.

The ethylene oxide (EO) and propylene oxide (PO) reactants are commercially available chemicals which may be obtained from many sources. Mixtures of EO and PO may also be employed as reactants, either added sequentially or mixed together.

It should be understood that the number of moles of EO or PO reacted at each of the two reactive sites of the 2,5-dimercapto-1,3,4-thiadiazole molecule will not necessarily always be the same. For instance, as shown in Equation (A), above, (where 5 moles of PO were reacted), it does not necessarily follow that 3 moles of PO will react at one site and 2 moles will react at the other site. Instead, it may be likely that in some instances only 1 mole, or may be none, may react at the one site and 4 moles, or even 5 moles, may react at the other site. Furthermore, it should be understood that the total number of EO and PO moles on each resulting adduct molecules will be a statistical distribution. Thus, the sum of y and z in Formula (I) represents the average number of EO and PO units per adduct and that the actual number on any given adduct may be less or greater than that sum. That is, when $y+z=10$, it is meant that ten moles of EO or PO have been reacted per mole of the desired 1,3,4-thiadiazole. Preferably, it is desired to employ from about 5 to about 20 moles of EO or PO per one mole of the desired 1,3,4-thiadiazole. More preferably, it is desired to use from about 5 to about 10 moles per mole of the desired 1,3,4-thiadiazole.

Any conventional reaction conditions designed to produce these poly(oxyalkylated) 1,3,4-thiadiazole adducts may be employed in the synthesis of the present compounds and the present invention is not intended to be limited to any particular reaction conditions. Advantageously and preferably, the present compounds may be made according to the reaction illustrated by Equation (A) in the presence of an inert solvent such as dioxane and dimethyl formamide (DMF) and an alkaline catalyst like potassium hydroxide or sodium methylate. However, the use of a solvent and a catalyst is only desirable, and not necessary. The reaction temperature and time will both depend upon many factors including the specific reactants and apparatus employed. In most situations, reaction temperatures from about 80° C. to about 140° C., preferably from about 85° C. to about 110° C. may be employed. Reaction times from about 30 minutes to about 600 minutes may be employed. The reaction may preferably be carried out at atmospheric pressure or under pressure from about 10 to about 100 psig or more, if desired. The desired adduct product may be recovered from the reaction mixture by any conventional means, for example, evaporation of the solvent, filtration, extraction, recrystallization or the like.

It should be noted that while the reaction illustrated by Equation (A) is the preferred method for preparing the compounds of the present invention, other synthetic methods may also be employed.

Also, in accordance with the present invention, it has been found that the compound of Formula (I), above, may be utilized as effective corrosion inhibitors. In practicing the process of the present invention, metal surfaces are contacted with an effective corrosion-inhibiting amount of one or more of these compounds. "Metal surfaces" which may be protected by the corrosion-inhibition properties of the compounds of the present invention include ferrous and non-ferrous metals such as cast iron, steel, brass, copper, solder, aluminum, and other materials commonly used with corrosive liquids. It is understood that the term "effective corrosion-inhibiting amount" as used in the specification and claims herein is intended to include any amount that will prevent or control the corrosion on said metal surfaces. Of course, this amount may be constantly changing because of the possible variations in many parameters. Some of these parameters may include the specific corrosive material present; the specific compound used; the specific metal to be protected against corrosion; the salt and oxygen content in the system; the geometry and capacity of the system to be protected against corrosion; flow velocity of the corrosive material; temperature and the like.

One preferred use of the corrosion inhibitors of the present invention is in aqueous acidic solutions or baths which are in contact with metal surfaces. Such acidic solutions include mineral acid solutions such as sulfuric acid, hydrochloric acid, or the like. These acidic solutions may be used for acid-pickling baths for the surface cleaning of metals or in similar processes. The preferred amount of this corrosion inhibitor in such acid solutions is preferably at least 0.005% by weight of the solution; more preferably, from about 0.01% to about 0.5% by weight of the solution or bath.

Acid pickling solutions or baths are commonly used to remove rust or scale from the surfaces of metals. In commercial operations, this rust or scale is removed by immersing a metal sheet, plate, bar, or the like in the acid pickling solution. The acid solution attacks and dissolves the rust or scale. Once the scale is dissolved, the acid is then free to further attack the metal surface. In order to reduce this attack on the metal, corrosion inhibitors are added to the pickling acid solution.

The compounds of this invention may be used for other corrosion protection applications beside the abovementioned preferred applications. In addition, these compounds may be employed with other known corrosion inhibitors and/or with inert substances such as fillers, dispersing agents, and the like.

The following examples further illustrate the present invention. All parts and percentages employed herein are by weight unless otherwise indicated.

EXAMPLE 1

2,5-Dimercapto-1,3,4-Thiadiazole.6 Ethylene Oxide 2,5-Dimercapto-1,3,4-thiadiazole [15 g (0.1 moles)] was placed in a flask fitted with a dry-ice condenser, thermometer and a dropping funnel with 0.5 g of its disodium salt as catalyst and heated to 90° C. in an oil bath. Liquid ethylene oxide was dropped in causing an exothermic reaction and forming a yellow liquid product. The temperature was held at 120°-130° C. while [66 g (1.5 moles)] of EO was added. After heating four hours, the unreacted EO was swept out in a $N_2$ stream and 35.5 g of semi-solid product collected with an elemental analysis as follows:

|  | C | H | N | S |
|---|---|---|---|---|
| Calculated for DMTD . 6EO: | 40.63 | 6.32 | 6.77 | 23.24 |
| Found: | 39.98 | 6.01 | 7.15 | 23.92 |

EXAMPLE 2

2,5-Dimercapto-1,3,4-Thiadiazole.12 Ethylene Oxide

Dimercapto-1,3,4-thiadiazole [37.5 g (0.25 mole)] was dissolved in 200 ml of dimethylformamide (DMF) in a 3-neck flask as above. KOH (1.2 g) was added and the mixture heated to 116° C. while dropping in 44 g of EO over 3 hours to give a yellow solution. The entire mixture was transferred to a pressure vessel. An additional 100 ml of DMF and 2.5 g of KOH was added. After purging with $N_2$, the vessel was heated to 90°-95° C. while adding [176 g (4 moles) of EO over 1.5 hours. The mixture was post-reacted one hour at 95° C. The mixture was transferred to a flask and the solvent and unreacted EO was removed under vacuum to give 254 g of product, a viscous brown liquid with an elemental analysis as follows:

|  | C | H | N | S |
|---|---|---|---|---|
| Calculated for DMTD . 12EO: | 46.06 | 7.14 | 4.13 | 14.19 |
| Found: | 45.64 | 8.19 | 3.66 | 8.77 |

EXAMPLE 3

2,5-Dimercapto-1,3,4-Thiadiazole.4 Propylene Oxide

A pressure vessel was charged with [75 g (0.5 moles)] of 2,5-dimercapto-1,3,4-thiadiazoled, 4.5 g of potassium hydroxide and 300 ml of dioxane. The vessel was purged with nitrogen gas, heated to 108° C. and [295 g (5 moles)] of propylene oxide fed in over a two hour period. The temperature was held at 115° C.±5 while the pressure varied from 5 to 40 psi. The mixture was post-reacted one hour to give a turbid orange solution. Removal of the solvent and unreacted PO under vacuum left 194 g of product with an elemental analysis as follows:

|  | C | H | N | S |
|---|---|---|---|---|
| Calculated for DMTD . 4PO: | 43.98 | 6.81 | 7.33 | 25.13 |
| Found: | 43.81 | 6.72 | 7.17 | 24.76 |

EXAMPLE 4

2,5-Dimercapto-1,3,4-Thiadiazole.6 Propylene Oxide

Dimethylformamide (200 ml) was placed in a 3-necked flask with dimercapto-1,3,4-thiadiazole [37.5 g (0.25 moles)]. Potassium hydroxide (1.4 g) was added and the mixture heated to 110° C. Propylene oxide [58 g (1 mole)] was added over 2 hours. This reaction mixture was poured into a pressure vessel with an additional 100 ml of DMF and 3.5 g KOH. The vessel was sealed, purged with $N_2$ and heated to 90° C. while adding [232 g (4 moles)] of PO over 1.5 hours. The mixture was post-reacted one hour at 90° C. The mixture was transferred to a flask and the solvent and unreacted PO was removed under vacuum leaving 126 g of product, a brown liquid with an elemental analysis as follows:

|  | C | H | N | S |
|---|---|---|---|---|
| Calculated for DMTD . 6PO: | 47.78 | 7.62 | 5.57 | 19.13 |
| Found: | 46.63 | 7.78 | 7.80 | 15.75 |

EXAMPLE 5

2,5-Dimercapto-1,3,4-Thiadiazole.5 Propylene Oxide.6 Ethylene Oxide 2,5-Dimercapto-1,3,4-thiadiazole [75 g (0.5 moles)] was placed in a pressure vessel with 300 ml of dimethylformamide and 2.5 g of sodium methylate. After purging with $N_2$ [174 g (3 moles)] of propylene oxide were added over one hour at a temperature of 88° C. while the pressure varied from 20–60 psi. The mixture was post-reacted 2.5 hours at 80°–85° C. and 35 psi. Ethylene oxide [132 g (3 moles)] was then added over 30 minutes at 80° C. with a pressure of 15 psi and post-reacted at 90° C. and a pressure of 15–60 psi.

The reaction mixture was neutralized with acetic acid, filtered and the solvent and unreacted PO and EO were removed under vacuum to give 241 g of orange-brown liquid with an elemental analysis as follows:

|  | C | H | N | S |
|---|---|---|---|---|
| Calculated for DMTD . 5PO . 6EO: | 49.13 | 8.81 | 3.95 | 13.37 |
| Found: | 46.30 | 7.60 | 5.33 | 14.21 |

EXAMPLE 6

Stock solutions of the inhibitors were made by weighing 10 grams of the test compound into a 100 ml volumetric flask and filling with either ethanol or dimethylformamide to give a 10% weight/volume concentrate. This concentrate was pipetted into weighed 500 ml flasks and acid added to give 500 g of solution of required inhibitor concentration.

Coupons measuring about 76 mm × 18 mm × 1.5 mm made from 1010 steel were sanded with 240 grit paper, degreased in acetone and weighed after drying. After the tests, the coupons were scrubbed with pumice, rinsed with water, acetone and re-weighed after drying. All runs were made in duplicate and average values reported. The tests were run in glass flasks and the coupons were suspended from glass rods, two per flask.

The tests at ambient temperature (75° F.±3° F.) were run for 24 hours in 10% hydrochloric acid and in 20% sulfuric acid. The high temperature tests, 190° F.±1° F., were run for three hours in 10% hydrochloric acid and in 5% sulfuric acid.

In Tables 1–4, below, the corrosion rate (in mills per year—MPY) and the percent inhibition (%I) are given. These results were determined by the following formulae:

$$MPY = \text{Corrosion Rate} = \frac{\text{wt. loss of coupon (mg)} \times 534}{\text{coupon area (in}^2\text{)} \times \text{coupon density} \times \text{test duration (hr)}}$$

$$\%I = \%\text{Inhibition} = \frac{\text{wt. loss (uninhibited)} - \text{wt. loss (inhibited)}}{\text{wt. loss (uninhibited)}} \times 100$$

The symbols used in the Tables stand for:
DMTD = 2,5-dimercapto-1,3,4-thiadiazole
EO = ethylene oxide
PO = propylene oxide The above equation for MPY may be found in NACE Standard Test Method 01-69: "Laboratory Corrosion Testing of Metals for Processing Industries".

As can be seen from the results in these Tables, the corrosion inhibitors of the present invention that were tested are all effective corrosion inhibitors in aqueous acidic solutions.

TABLE 1

| | CORROSION RATE IN MPY IN 10% HCl AT 75° F. | | | | | |
|---|---|---|---|---|---|---|
| Compound | 1000 ppm | (% I) | 500 ppm | (% I) | 250 ppm | (% I) |
| Blank | 463 | | 463 | | 463 | |
| DMTD . 6EO | 9.5 | (97.9) | 9.4 | (98.0) | | |
| | 9.4 | (98.0) | | | | |
| DMTD . 12 EO | 27.3 | (94.1) | 27.9 | (94.0) | — | |
| DMTD . 4PO | 18.4 | (96.6) | 20.8 | (95.5) | — | |
| DMTD . 6PO | 11.3 | (97.6) | 10.2 | (97.68) | 11.6 | (97.5) |
| DMTD. 5PO . 6EO | 12.1 | (97.4) | 11.2 | (97.6) | | |

TABLE 2

| | CORROSION RATE IN MPY IN 20% $H_2SO_4$ AT 75° F. | | | |
|---|---|---|---|---|
| Compound | 500 ppm | (% I) | 500 ppm | (% I) |
| Blank | 241.5 | | 241.5 | |
| DMTD . 6EO | 5.1 | (97.9) | 5.0 | (97.9) |
| DMTD . 12 EO | 12.3 | (94.9) | 11.8 | (95.1) |
| DMTD . 4PO | 5.4 | (97.8) | 5.1 | (97.9) |
| DMTD . 6PO | 4.6 | (98.1) | 4.9 | (98.0) |
| DMTD. 5PO . 6EO | 5.9 | (97.6) | 5.0 | (97.9) |

TABLE 3

| CORROSION RATE IN MPY IN 10% HCl AT 190° F. | | |
|---|---|---|
| Compound | 1000 ppm | (% I) |
| Blank | 57,982 | |
| DMTD . 6EO | 1,499 | (97.4) |
| DMTD . 12EO | 2,637 | (95.5) |
| DMTD . 4PO | 21,740 | (62.5) |
| DMTD . 6PO | 5,788 | (90.0) |
| DMTD . 5PO . 6EO | 3,445 | (94.1) |

TABLE 4

| CORROSION RATE IN MPY IN 5% $H_2SO_4$ AT 190° F. | | |
|---|---|---|
| Compound | 1000 ppm | (% I) |
| Blank | 14,079 | |
| DMTD . 6EO | 214 | (98.5) |
| DMTD . 12EO | 611 | (95.7) |
| DMTD . 4PO | 1,041 | (92.6) |
| DMTD . 6PO | 570 | (96.0) |
| DMTD . 5PO . 6EO | 328 | (97.7) |

What is claimed is:

1. An acid metal-treating bath comprising an acid and an effective corrosion-inhibiting amount of a poly (oxyalkylated) 1,3,4-thiadiazole having a formula:

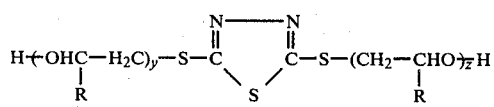

wherein each R is individually selected from either H or CH₃; and the sum of y and z is from 2 to about 30.

2. The acid bath of claim 1 wherein the acid comprises sulfuric acid or hydrochloric acid.

3. The acid bath of claim 1 wherein the sum of y and z is from about 5 to about 20.

4. A process for inhibiting corrosion of metal surfaces caused by corrosive aqueous solutions, which comprises contacting said metal surfaces with an effective corrosion-inhibiting amount of a poly(oxyalkylated) 1,3,4-thiadiazole having a formula:

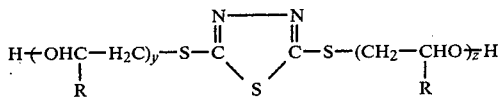

wherein each R is individually selected from either H or CH₃; and the sum of y and z is from 2 to about 30.

5. The process of claim 4 wherein each R is H.

6. The process of claim 4 wherein each R is CH₃.

7. The process of claim 4 wherein at least one R is H and CH₃.

8. The process of claim 4 wherein the sum of y and z is from about 5 to about 20.

9. A process of inhibiting the corrosion of metals which come into contact with an acid solution, which comprises contacting the surface of the metal to be inhibited against corrosion with the corrosion-inhibited acid metal-treating bath of claim 1.

10. The process of claim 9 wherein the acid in acid bath comprises sulfuric acid or hydrochloric acid.

* * * * *